United States Patent
Iinuma

(10) Patent No.: US 9,999,612 B2
(45) Date of Patent: Jun. 19, 2018

(54) PPARS AGONIST ACTIVITY ENHANCING DRUG

(71) Applicants: Tsujimoto Chemical Co., Ltd., Osaka-shi, Osaka (JP); Munekazu Iinuma, Gifu (JP)

(72) Inventor: Munekazu Iinuma, Gifu (JP)

(73) Assignee: TSUJIMOTO CHEMICAL CO., LTD., Osaka (JP)

( * ) Notice: Subject to any disclaimer, the term of this patent is extended or adjusted under 35 U.S.C. 154(b) by 0 days. days.

(21) Appl. No.: 15/260,434

(22) Filed: Sep. 9, 2016

(65) Prior Publication Data

US 2016/0374986 A1  Dec. 29, 2016

Related U.S. Application Data

(62) Division of application No. 14/814,013, filed on Jul. 30, 2015, which is a division of application No. 14/388,012, filed as application No. PCT/JP2013/058107 on Mar. 21, 2013, now abandoned.

(30) Foreign Application Priority Data

Mar. 27, 2012 (JP) .................. 2012-071175
Mar. 27, 2012 (JP) .................. 2012-071178

(51) Int. Cl.
  *A61K 31/366*  (2006.01)
  *C07D 309/32*  (2006.01)
  *A61K 9/00*    (2006.01)

(52) U.S. Cl.
  CPC .......... *A61K 31/366* (2013.01); *A61K 9/0053* (2013.01); *C07D 309/32* (2013.01)

(58) Field of Classification Search
  CPC ................................................. A61K 31/366
  USPC ....................................................... 514/460
  See application file for complete search history.

(56) References Cited

U.S. PATENT DOCUMENTS

2013/0136836 A1* 5/2013 Putter ............... A23L 29/30
                                                  426/536

FOREIGN PATENT DOCUMENTS

| JP | 63-057583 | 3/1988 |
| JP | 2007-112720 | 5/2007 |
| JP | 2009-091261 | 4/2009 |
| JP | 2009-091262 | 4/2009 |
| WO | 2007/007757 | 1/2007 |

OTHER PUBLICATIONS

PCT, International Search Report, PCT/JP2013/058104 (dated Apr. 16, 2013).
PCT, International Preliminary Report on Patentability, PCT/JP2013/058104 (dated Oct. 9, 2014).
Abe et al., "Studies on the Synthesis of Massoi-lactone and its Homologues. Part II. Synthesis of Nonyn-1-ol-4-carboxylic acid-1-lactone (Massoi-lactone)", Bulletin of the Chemical Society of Japan, vol. 29, No. 1, pp. 88-90 (Jan. 1956).
Reich et al., "Organoselenium Chemistry. Conversion of Ketones to Enones by Selenoxide Syn Elimination", Journal of the American Chemical Society, vol. 97, No. 19, pp. 5434-5447 (Sep. 17, 1975).
Carlson et al., "Synthetic of Substituted 5,6-Dihydro-2H-pyran-2-ones. Propiolic Acid Dianion as a Reactive Three-Carbon Nucleophile", Journal of Organic Chemistry, vol. 40, No. 11, pp. 1610-1616 (1975).
Yoshida et al., "A New Method for Synthesis of $\alpha,\beta$-Unsaturated $\zeta$-Lactones via Michael Addition Using Methyl (Phenylsulfinyl) Acetate", Chemistry Letters, the Chemical Society of Japan, pp. 1587-1590 (1982).
US, Non-Final Office Action, U.S. Appl. No. 14/814,013 (Jan. 20, 2016).

* cited by examiner

*Primary Examiner* — Nizal S Chandrakumar
(74) *Attorney, Agent, or Firm* — Thompson Hine LLP

(57) ABSTRACT

A lifestyle disease improving drug is disclosed that enhances PPAR$\alpha$, $\delta$ and $\gamma$ agonist activities that includes a compound having the lactone structure in accordance with the chemical formula 6-alkyl-5,6-dihydro-2H-pyran-2-one, the alkyl containing 4, 5, or 6 carbons. Methods for enhancing PPAR$\alpha$, $\gamma$ and $\delta$ agonist activities in vertebrates or medically treating a vertebrate are disclosed. The methods include providing a composition of an active ingredient, the lifestyle disease improving drug, in a biologically acceptable medium and administering an effective amount of the composition to a vertebrate.

8 Claims, 6 Drawing Sheets

US 9,999,612 B2

PPARS AGONIST ACTIVITY ENHANCING DRUG

RELATED APPLICATIONS

This application is a divisional of application Ser. No. 14/814,013, filed Jul. 30, 2015, which is a divisional of application Ser. No. 14/388,012, filed Sep. 25, 2014, now abandoned, which was the National Stage filing of International PCT/JP2013/058104, filed Mar. 21, 2013, the entirety of which is herein incorporated by reference.

TECHNICAL FIELD

The present invention relates to drugs capable of contributing to enhancement of agonist activity for PPARs, by which improvement of lifestyle diseases, particularly metabolic syndromes can be enhanced.

BACKGROUND ART

As PPARs (peroxisome proliferator-activated receptor) in bodies of vertebrates like humans, PPARα and PPARγ are currently known, and PPARδ (β) has been recently found. In the present Specification, these are collectively called PPARs.

Among them, it is known that PPARα corresponds to hypertension and arteriosclerosis resulting from adhesion of neutral fat to a vessel wall and has a function to activate lipase, which is an enzyme for decomposing neutral fat. Some medicines for the above-mentioned function have been already developed.

In addition, PPARγ draws attention as a receptor which can enhance insulin sensitivities of tissues, and it is known that diabetes or the like can be prevented by appropriately activating PPARγ to improve insulin resistance. Some medicines for this purpose have been developed.

LIST OF CITATION

Patent Document

Patent Document 1: JP 2007-112720 A1
Patent Document 2: WO 2007/007757

SUMMARY OF INVENTION

Technical Problem to be Solved

Patent Document 1 is an invention related to a medicine primarily for enhancing the agonist activity for PPARα, which includes a fibrate-based drug as an active ingredient in order to contribute to prevention or treatment of metabolic syndromes. Patent Document 2 is an invention related to a medicine primarily for enhancing the sensitivity of PPARγ.

As mentioned above, the known PPARs have a plurality of above-mentioned subclasses of α, γ and δ, each of which is supposed to have a specific active function. However, in pathological view, there are more complex chained mechanisms. Specifically, hyperlipidemia results from neutral fat adhering to a vessel wall, and this fat is also related to blood glucose. That is, if the blood glucose cannot be appropriately controlled, intracellular fat is accumulated and causes obesity, which is one of the recently controversial characteristics of metabolic syndrome. Thus, symptoms of hyperlipidemia, diabetes and metabolic syndrome are connected with each other, and even if only one symptom of them is targeted, they are not radically treated. That is a problem. In particular, although metabolic syndrome shows a phenomenon that a symptom of obesity is exhibited by fat excessively accumulated in fat cells universally existing everywhere in a body, it has been elucidated that PPARδ is promising as a substance showing effective agonist activity on the fat cells universally existing in such a manner. However, in fact, innovative chemical structures, compounds or extracts as medicines for effectively activating PPARδ have not been proposed yet.

An object of the present invention is to disclose a medicine which can activate PPARδ which is supposed to be effective in metabolic syndrome treatment conventionally considered to be difficult, to disclose a medicine which can concurrently enhance both PPARα and PPARγ agonist activities and also be effective in treatments of hyperlipidemia and diabetes, and to disclose a medicine which can be utilized in total improvement and treatment for improving lifestyle diseases.

Solution to Problem

In the present invention, the composition enhancing the agonist activity for PPARs was sought in naturally-derived medium chain fatty acids and their derivatives. The medium chain fatty acids and their derivatives were focused for the following inference. That is, higher animals like humans take, as foods, higher fatty acids (long chain fatty acids) such as palmitic acid, stearic acid, linoleic acid, linolenic acid, arachidonic acid, eicosapentaenoic acid or docosahexaenoic acid contained in plants and animals, metabolize them with β-oxidation in the body, and consume them as energy sources. In addition to the application as the energy sources, some fatty acids such as arachidonic acid are once taken into the body as starting materials for important biological activity and used for maintaining vital phenomenon phenomena while being free as required. In addition, eicosapentaenoic acid, docosahexaenoic acid and the like are also supposed to be associated with prevention of lifestyle diseases such as hypertension. These higher fatty acids are decomposed, through medium chain fatty acids such as octanoic acid, decanoic acid and dodecanoic acid as intermediates by β-oxidation, into short chain fatty acids such as acetic acid, propionic acid and butanoic acid by further β-oxidation, but conventionally humans have not been supposed to utilize medium chain fatty acids. Accordingly, while higher fatty acids are directly associated with vital phenomenon phenomena as nutrients and physiologically active substances so that they have been studied well, the importance of medium chain fatty acids has not been enough discussed enough. However, each of some animals, like insects, and plants successfully utilize the medium chain fatty acids so as to maintain its their species as members in the ecosystem. In particular, pheromones of insects contain a large amount of medium chain fatty acids and their derivatives, and royal jelly of bees and constituents of a queen bee substance also contain the medium chain fatty acid derivatives. In addition, humans take bee products as foods, and have been utilized humans utilize not only honey but also propolis, pollen dumpling, royal jelly and bees wax as foods. Thus, the inventors focused on medium chain fatty acids such as decanoic acid and decenoic acid contained in royal jelly, and expected that these derivatives had some positive impacts on the physiological activity of humans. As a further basis, human must have utilized a medium chain fatty acid at least once in the course of evolution, and it was also focused that a receptor of medium chain fatty acid remained as a trace even now, through evolution.

In addition, as components which exhibit nuclear receptors PPARα agonist activity, PPARγ agonist activity and PPARδ agonist activity, the research was advanced on medium chain fatty acid ester bodies among the medium chain fatty acids. As a result, it was found that a medium chain fatty acid with a lactone structure (γ, δ, ε) had the activity.

[Chemical formula 1]

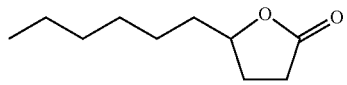

[Chemical formula 2]

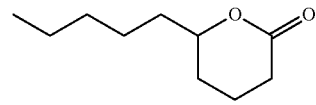

[Chemical formula 3]

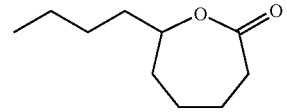

When activities of the above-described three lactone structures, γ-decanolactone (Chemical formula 1), δ-decanolactone (Chemical formula 2) and ε-decanolactone (Chemical formula 3) were verified, the δ-decanolactone (Chemical formula 2) showed a relatively strong activity, and as a size of the lactone ring, six-membered ring was suitable.

Subsequently, compositions having the following structures were prepared and the activity of them was studied in order to verify the influences of the aliphatic chain lengths.
    δ-hexanolactone (6-methyltetrahydro-2H-pyran-2-one),
    δ-octanolactone (6-propyltetrahydro-2H-pyran-2-one),
    δ-nonanolactone (6-butyltetrahydro-2H-pyran-2-one),
    δ-decanolactone (6-pentyltetrahydro-2H-pyran-2-one),
    δ-undecanolactone (6-hexyltetrahydro-2H-pyran-2-one),
    δ-docecanolactone (6-heptyltetrahydro-2H-pyran-2-one),
    δ-tridecanolactone (6-octyltetrahydro-2H-pyran-2-one), and
    δ-tetradecanolactone (6-nonyltetrahydro-2H-pyran-2-one).

As a result, the δ-nonanolactone (carbon number in the side chain: C4, Chemical formula 4), δ-decanolactone (carbon number in the side chain: C5, Chemical formula 5) and δ-undecanolactone (carbon number in the side chain: C6, Chemical formula 6) respectively showed the strong agonist activity. The agonist activity was observed not only in PPARδ as originally expected, but also in PPARα and PPARγ.

[Chemical formula 4]

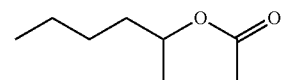

[Chemical formula 5]

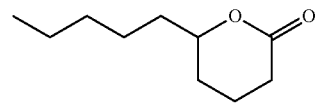

[Chemical formula 6]

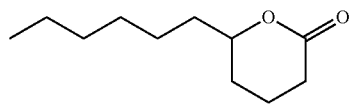

Subsequently, in order to enhance the activity intensity, α and β positions of each δ lactone ring were substituted for double bonds to obtain 6-butyl-5,6-dihydro-2H-pyran-2-one (Chemical formula 7), 6-pentyl-5,6-dihydro-2H-pyran-2-one (Chemical formula 8) and 6-hexyl-5,6-dihydro-2H-pyran-2-one (Chemical formula 9).

[Chemical formula 7]

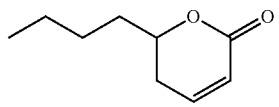

[Chemical formula 8]

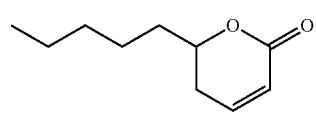

[Chemical formula 9]

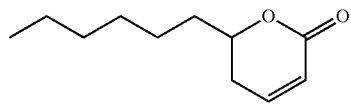

The present invention is directed to an application for enhancing the PPARs agonist activity of the known compounds comprising Chemical formulae 7 and 8 (carbon number C9, C10), and a structure and an application of novel compounds having a lactone structure comprising Chemical formula 9 (C11). That is, these compounds have efficacies to enhance the PPARα, δ and γ agonist activities and are utilized as an improving drug for lifestyle diseases.

A synthetic method for each compound is as below.
(Chemical Formula 7)

A solution of diisopropylamine (1.21 ml, 8.63 mmol) in THF (tetrahydrofuran) (33 ml) was cooled to −78° C. under a nitrogen atmosphere, to which a butyllithium-hexane solution (1.1 M, 7.27 ml, 8.00 mmol) was added, and 10 minutes later, a solution of 6-butyltetrahydro-2H-pyran-2-one (1.00 g, 6.40 mmol) in THF (2 ml) was dropped, and stirred for 10 minutes. Subsequently, a solution of phenylselenyl chloride (1.19 g, 6.21 mmol) in THF (5 ml) was slowly dropped, and stirred at −78° C. for another 30 minutes, to which a saturated ammonium chloride solution was dropped to terminate the reaction. The reaction mixture was extracted with hexane, and its organic layer was dried with anhydrous sodium sulfate and distilled off under reduced pressure. The residue was purified by a silica gel column chromatography (hexane-ethyl acetate 10:1-8:1-6:1) so as to obtain a pure phenylselenide (842 mg, 42%) as a diastereomer mixture.

A solution of phenylselenide (842 mg, 2.70 mmol) in THF (14 ml) was cooled to 0° C., to which sodium bicarbonate (454 mg, 5.40 mmol) was added, and 30% hydrogen peroxide water (1.53 g, 45.0 mmol) was slowly dropped while stirring. This was stirred at 0° C. for another one hour, to which a sodium thiosulfate aqueous solution was added to terminate the reaction. The reaction mixture was extracted with chloroform, and its organic layer was dried with anhydrous sodium sulfate and distilled off under reduced pressure. The residue was purified by a silica gel column chromatography (hexane-ethyl acetate 5:1-4:1) so as to obtain a pure desired substance (257 mg, 62%).

A pale yellow oily substance; NMR $\delta_H$(CDCl$_3$): 6.89 (1H, ddd, J=10.2, 5.6, 3.6 Hz), 6.03 (1H, dt, J=10.2, 2.0 Hz), 4.43 (1H, m), 2.34 (2H, m), 1.80 (1H, m), 1.65 (1H, m), 1.50 (1H, m), 1.37 (3H, m), 0.92 (3H, t, J=7.0 Hz).

(Chemical Formula 8)

6-Pentyltetrahydro-2H-pyran-2-one (1.00 g, 5.87 mmol), diisopropylamine (1.08 ml, 7.71 mmol), a butyllithium-hexane solution (1.0 M, 6.48 ml, 6.48 mmol), phenylselenyl chloride (1.71 g, 8.93 mmol) were reacted, post-treated and purified under the same conditions to obtain a pure phenylselenide (1.39 g, 73%).

Phenylselenide (1.39 g, 4.27 mmol), sodium bicarbonate (719 mg, 8.56 mmol) and 30% hydrogen peroxide water (2.43 g, 71.4 mmol) were reacted, post-treated and purified in the same manner to obtain a pure desired substance (342 mg, 47%).

A pale yellow oily substance; NMR $\delta_H$(CDCl$_3$): 6.89 (1H, ddd, J=9.6, 5.6, 3.4 Hz), 6.02 (1H, dt, J=9.6, 1.2 Hz), 4.43 (1H, m), 2.34 (2H, m), 1.79 (1H, m), 1.65 (1H, m), 1.52 (1H, m), 1.41 (1H, m), 1.32 (4H, m), 0.90 (3H, t, J=6.6 Hz).

(Chemical Formula 9)

6-Hexyltetrahydro-2H-pyran-2-one (1.00 g, 5.43 mmol), diisopropylamine (0.99 ml, 7.06 mmol), a butyllithium-hexane solution (1.1 M, 5.92 ml, 6.51 mmol), phenylselenyl chloride (1.56 g, 8.15 mmol) were reacted, post-treated and purified under the same conditions to obtain a pure phenylselenide (1.04 g, 56%).

Phenylselenide (1.04 g, 3.06 mmol), sodium bicarbonate (512 mg, 6.09 mmol) and 30% hydrogen peroxide water (1.73 g, 50.9 mmol) were reacted, post-treated and purified in the same manner to obtain a pure desired substance (521 mg, 94%).

A pale yellow oily substance; NMR $\delta_H$(CDCl$_3$): 6.89 (1H, ddd, J=9.4, 4.8, 3.2 Hz), 6.03 (1H, dt, J=9.4, 2.0 Hz), 4.42 (1H, m), 2.34 (2H, m), 1.80 (1H, m), 1.65 (1H, m), 1.50 (1H, m), 1.30 (7H, m), 0.89 (3H, t, J=6.8 Hz).

[Among the above-mentioned three compounds, the compound shown in Chemical formula 7 has a composition known as an essential oil of lauraceous plants such as *Cryptocarya massoy*. In addition, the compound shown in Chemical formula 8 is also a known compound known as massoialactone contained in an unprocessed cane sugar. The compound shown in Chemical compound 9 is a novel compound.

Advantageous Effects of Invention

Lifestyle diseases such as hyperlipidemia, diabetes and metabolic syndrome can be comprehensively improved by appropriately administering the drug of the present invention.

DESCRIPTION OF EMBODIMENTS

Figure 1:
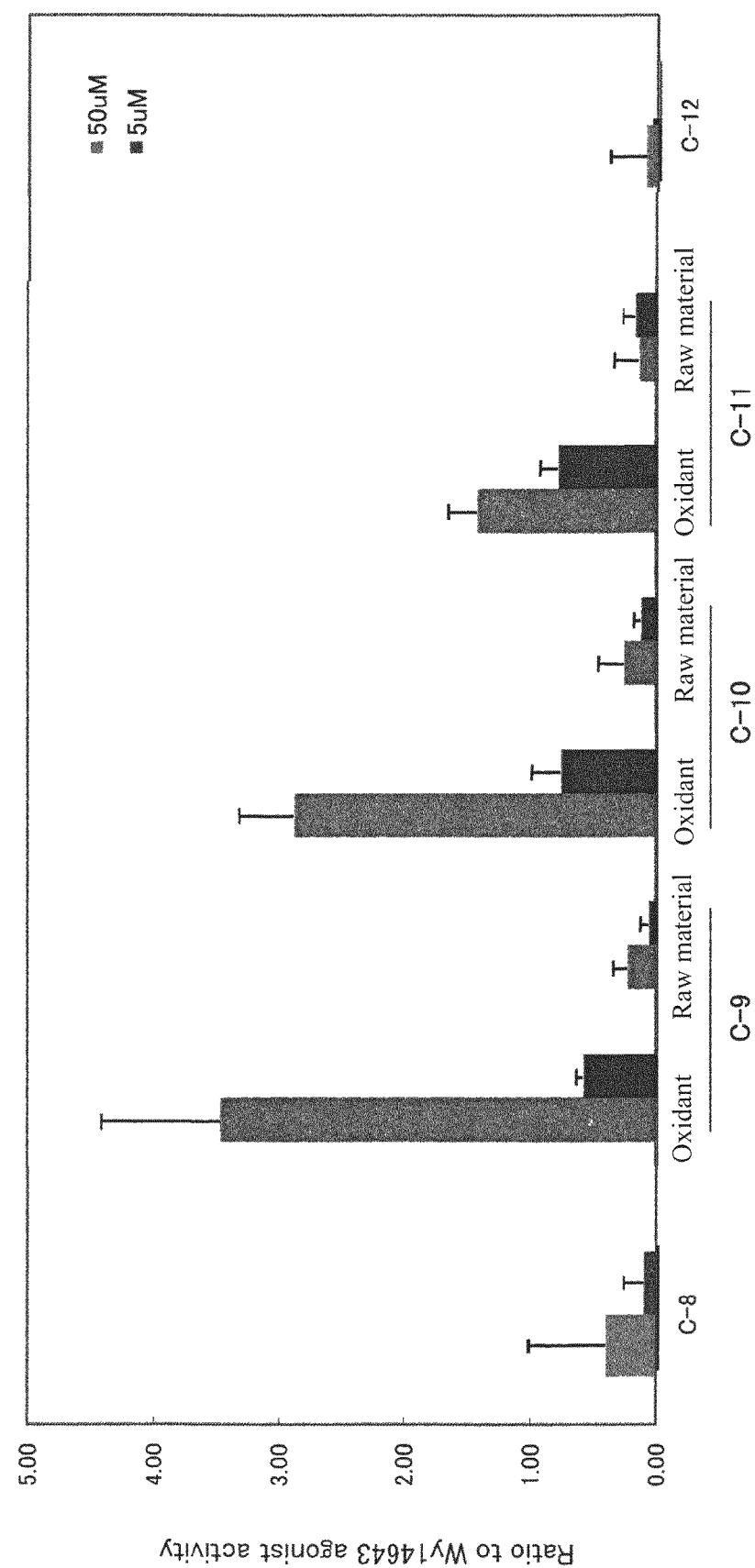
FIG. 1 is a graph evaluating the PPARα agonist activity of the compounds of the present invention with Comparative Examples.

The compounds having lactone structures shown in the present invention are suitable as preventive or ameliorating drugs for hyperlipidemia, ameliorating drugs for diabetes and preventive or ameliorating drugs for metabolic syndrome, and intended to be administered as oral agents. Embodiments of the oral agents may include a tablet, a granule, a powder, and a capsule in its original diluted oily state.

EXAMPLES

The agonist activities of PPARα, PPARδ and PPARγ, respectively, were visually verified by a reporter gene assaying method using COS-1 cells so as to evaluate them. The evaluation method is as below.

The COS-1 cells were collected by trypsinization, centrifuged (1000 rpm, 4° C., 3 min.), and then seeded on a 60 mm Petri dish for cultivation in a density of 6×10$^5$ cells/well. After cultivation at 37° C. under 5% CO$_2$ for 24 hours, cells were transformed using EFFECTENE® Transfection Reagent (QIAGEN®). EC buffer (150 ml), pPPARα-GAL4 (0.25 μg), pPPARδ-GAL4 (0.25 μg) or pPPARγ-GAL4 (0.25 μg), p17M2G (1 μg), pSEAP control vector (1 μg) were put into a 1.5 ml Eppendorf tube, to which 18 μl of Enhancer was added, and stirred by a vortex for 1 second. This was left to stand at room temperature for 3 minutes, to which 25 μl of Effectene was added, stirred by the voltex for 10 seconds, and left to stand at room temperature for 7 minutes. Simultaneously, the medium for transformation in the 60 mm Petri dish for cultivation was removed, to which 40 ml of medium was added to exchange the medium. Seven minutes later, 1 ml of medium was added to the Eppendorf tube, suspended twice, dropped to a 60 mm Petri dish for cultivation, and cultivated 37° C. under 5% CO$_2$ for 16 hours.

The cells were collected by trypsinization after 16 hours, centrifuged (1000 rpm, 4° C., 3 min.), and then suspended in 6 ml of medium, and seeded on a 96-well plate at 125 μl/well. The sample solution was added at 1.25 μl/well after 2-3 hours, and cultivated 37° C. under 5% CO$_2$ for 24 hours. Then the medium was collected at 25 μl/well, a secreted alkaline phosphatase (SEAP) activity was measured using GREAT ESCAPE™ SEAP (Clontech Laboratories, Inc.) kit. As the outline, 1× dilution buffer was added at 25 μl/well, mildly stirred, sealed with a scotch tape, and incubated at 65° C. for 30 minutes. Subsequently, it was cooled at 4° C., and returned to room temperature, then an assay buffer was added at 90 μl/well. It was left to stand at room temperature for 5 minutes, to which 10 μl of MUP solution was added at 10 μl/well. At room temperature, it was left to stand in a dark room for 1 hour, and then fluorescence intensity based on 4-methylumbelliferyl phosphate (Ex=360 nm, Em=460 nm) was measured.

In order to measure the activity for PPARα, luciferase activity measuring cocktail (Invitrogen) was added to other 96 well plate at 100 μl/well to measure the emission intensity. Compensation among each well was performed by dividing the measured value of the luciferase activity by the SEAP activity value.

FIG. 1 shows a graph evaluating the agonist activity for PPARα, the compounds shown as raw materials are the compounds represented by Chemical formulae 4 to 6 respectively before substitution for double bonds, and the compounds shown as oxidants are Chemical formulae. 7 to 9, i.e. C9 to C11 in which the α and β positions in the lactone ring of the raw material are substituted by double bonds, which are the compounds of the present invention. In addition, results of the compounds of the carbon numbers C8 and C12 were similarly shown as comparative examples. The structure of carbon number C8 lacks one side chain in the carbon number C9, and the structure of carbon number C12 adds one side chain to the carbon number C11, in which no double bond is provided. The carbon numbers C9 to C11 represents numbers of the carbon atoms in the compounds of Chemical formulae 4 to 6 and Chemical formulae 7 to 9. As shown in FIG. 1, a fibrate-based control substance WY14643 was used for evaluating the PPARα agonist activity, and a case of the 50 μM concentration was designated as a ratio 1.00. As the results, a sample of the same concentration as of the control substance showed higher activity than that of an indicator. Also, a sample adjusted to the one-tenth concentration, i.e. the 5 μM concentration showed activity almost equal to that of the control substance. In addition, since each oxidant showed an activity superior to that of the raw material, it was found that the compound in which the α and β positions in the lactone ring were substituted by double bonds had more preferable activity. In conclusion, all substances of the present invention can be expected as agents for enhancing the agonist activity for PPARα. Whereas, C8 shown as a comparative example can hardly be expected for the activity in a case of 5 μM dilution, and C12 did not show strong activity expected by the inventor in both cases of 50 μM and 5 μM.

Figure 2:
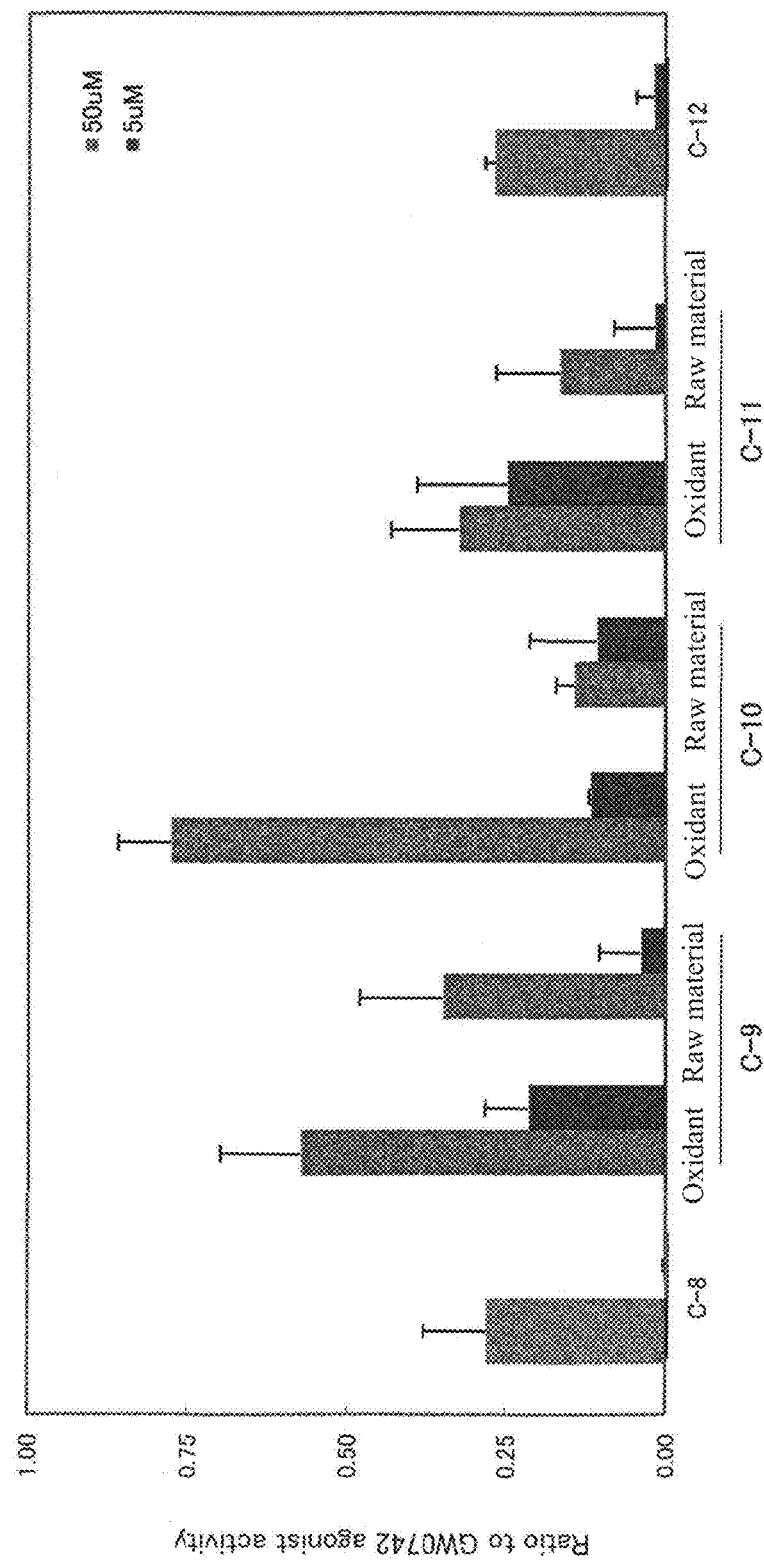
FIG. 2 is a graph evaluating the PPARδ agonist activity of the compounds of the present invention with Comparative Examples.

FIG. 2 shows a graph evaluating the PPARδ agonist activity, the same compounds as those shown in FIG. 1 are used, and 1 nM of GW0742 was used as the control substance. Concentrations of the samples to be evaluated are 50 μM and 5 μM. For this evaluation, although each oxidant had high concentration, it did not show higher activity than that of the control substance. However, the control substance has characteristics that when its concentration is lower than 1 nM, its activity is extremely lowered, meanwhile the activity is not improved even by heightening the concentration. In addition, these deserve enough evaluation as results of comparison between the control substance which shows remarkable characteristics among the known substances and the oxidants of the present invention. On the other hand, C8 and C12 shown as comparative examples showed little activity in the result at 5 μM rather than the value at the concentration of 50 μM.

Figure 3:
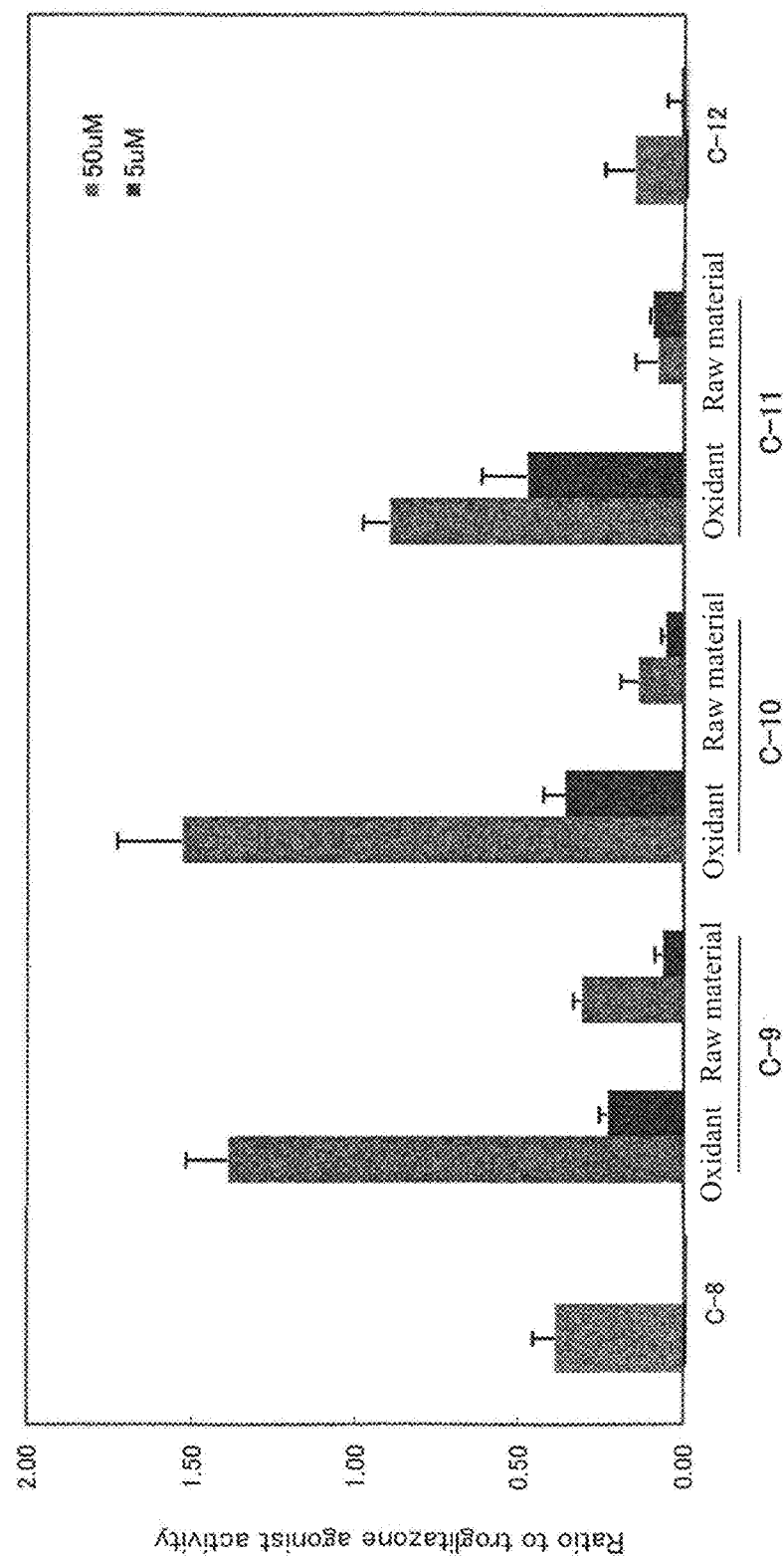
FIG. 3 is a graph evaluating the PPARγ agonist activity of the compounds of the present invention with Comparative Examples.

FIG. 3 shows a graph evaluating the PPARγ agonist activity, and 10 μM of Trogliazone was used as the control substance. Concentrations of the samples to be evaluated are 50 μM and 5 μM. When the concentrations of the oxidant samples were set to 50 μM, all oxidants showed higher activities than that of the control substance. Meanwhile, C8 and C12 shown as comparative examples showed only considerably lower activities than the values of C9 to C11 in the case of 50 μM concentration, and showed little activities in the case of 5 μM.

Since the present invention is originally directed to compounds having agonist activities for PPARα, δ and γ, oxidants of C9 to C11 (Chemical formulae 7 to 9) were identified based on the comprehensive evaluations of the activities of PPARα, δ and γ shown in FIGS. 1 to 3. That is, all of the compounds having the structures of C9 to C11 showed effective agonist activities for PPARs.

Figure 4:
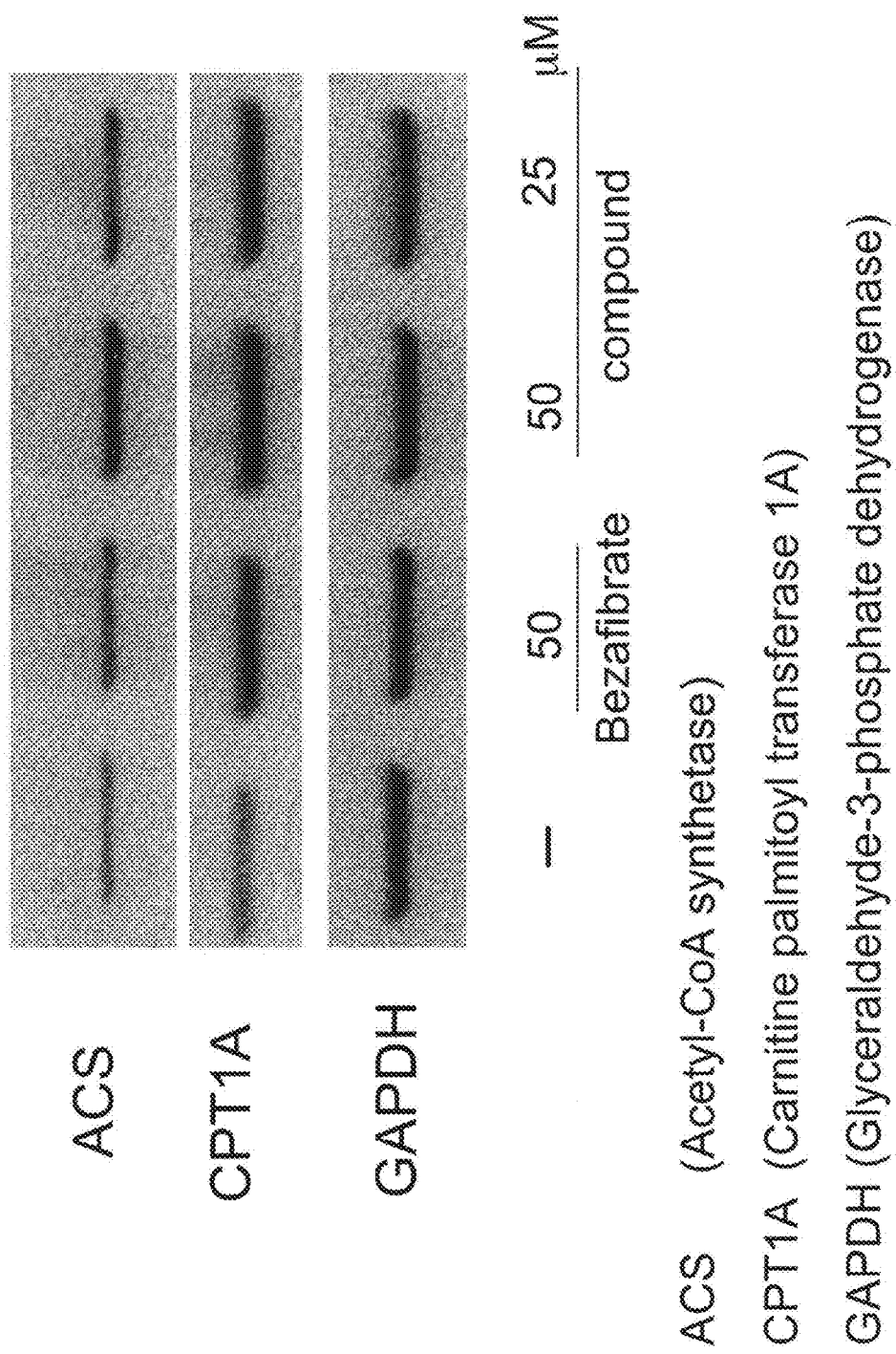
FIG. 4 is a photograph showing the agonist activity test of the compound of Chemical formula 9 for PPARα.

Next, a novel compound C11 was focused, and further activity tests using HepG2 cells were carried out. FIG. 4 shows a photograph verifying the agonist activity of C11 for PPARα and shows the influence on human liver cells. In the figure, GAPDH represents a housekeeping indicator, ACS represents expression of lipid metabolism gene, and CPT1A represents expression of lipolytic gene. As a drug for comparison, Bezafibrate known as PPARα agonist activity enhancer was used with 50 μM dilution, and the compound C11 of the present invention was used at concentrations of 50 μM and 25 μM. As a result, when the C11 compound was administered, a gene expression at least equal to or greater than that of Bezafibrate could be verified.

Figure 5:
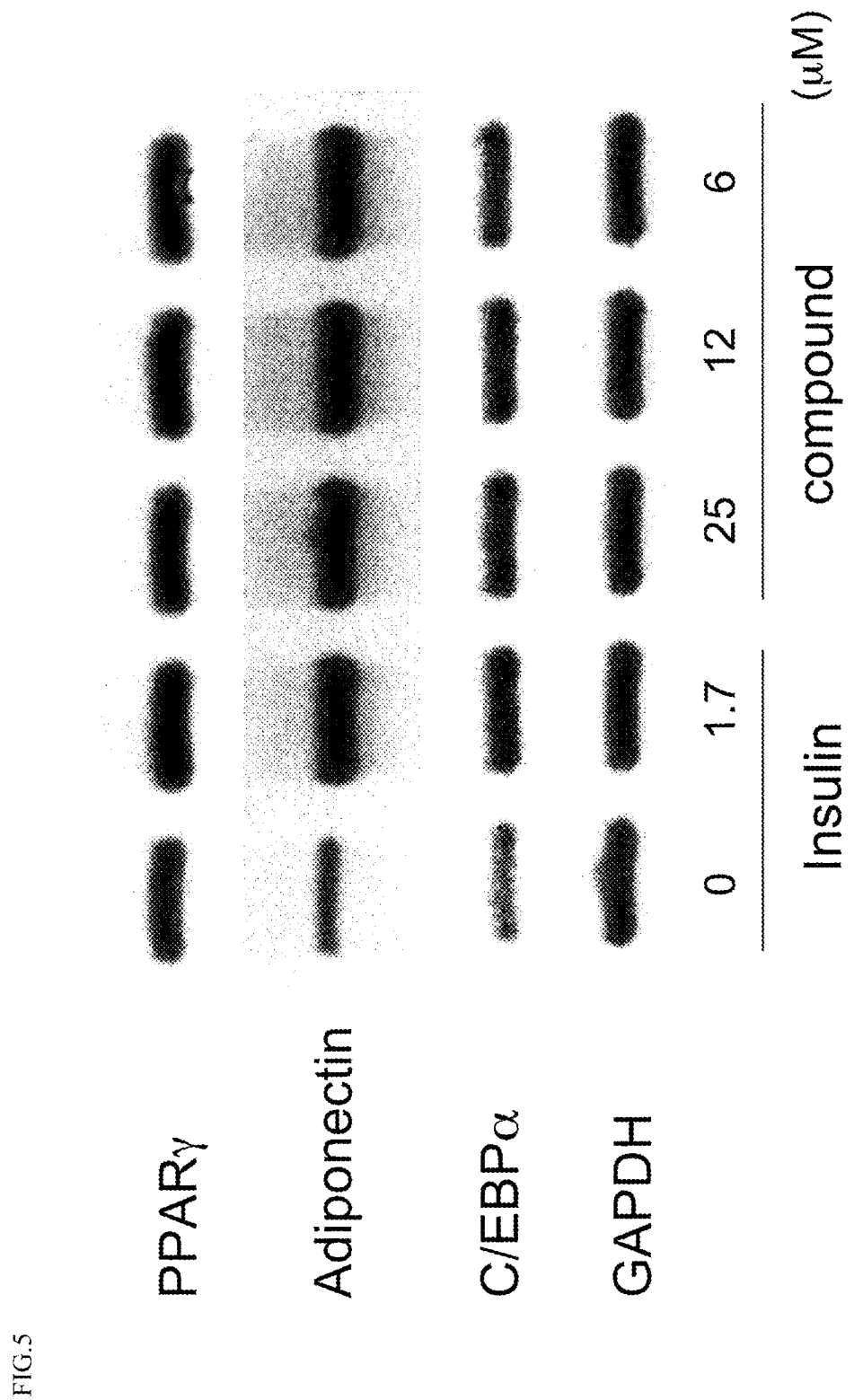
FIG. 5 is a photograph showing the agonist activity test of the compound of Chemical formula 9 for PPARδ.

Subsequently, an agonist activity test on fat cell differentiation induction-associated genes was similarly carried out for C11, and the results are shown in FIG. 5. In this test, the differentiation induction method using 3T3-L1 cells was conducted. For preparing samples, a plate having a total of 24 depressions of 6 lines×4 rows was used, and a known mouse fat cells was used to observe PPARγ agonist activities. In relation to 5 samples shown in the figure, in order from the right, a sample without insulin administration, a sample dosed with 1.7 μM of insulin, a sample dosed with 25 μM of C11 compound, a sample dosed with 12 μM of C11 compound and a sample dosed with 6 μM of C11 compound are shown. CAPDH is a housekeeping indicator, C/EBPα is a control, and Adiponectine is an expressed gene. As is obvious from the results, all samples dosed with C11 showed effective activities.

Figure 6:
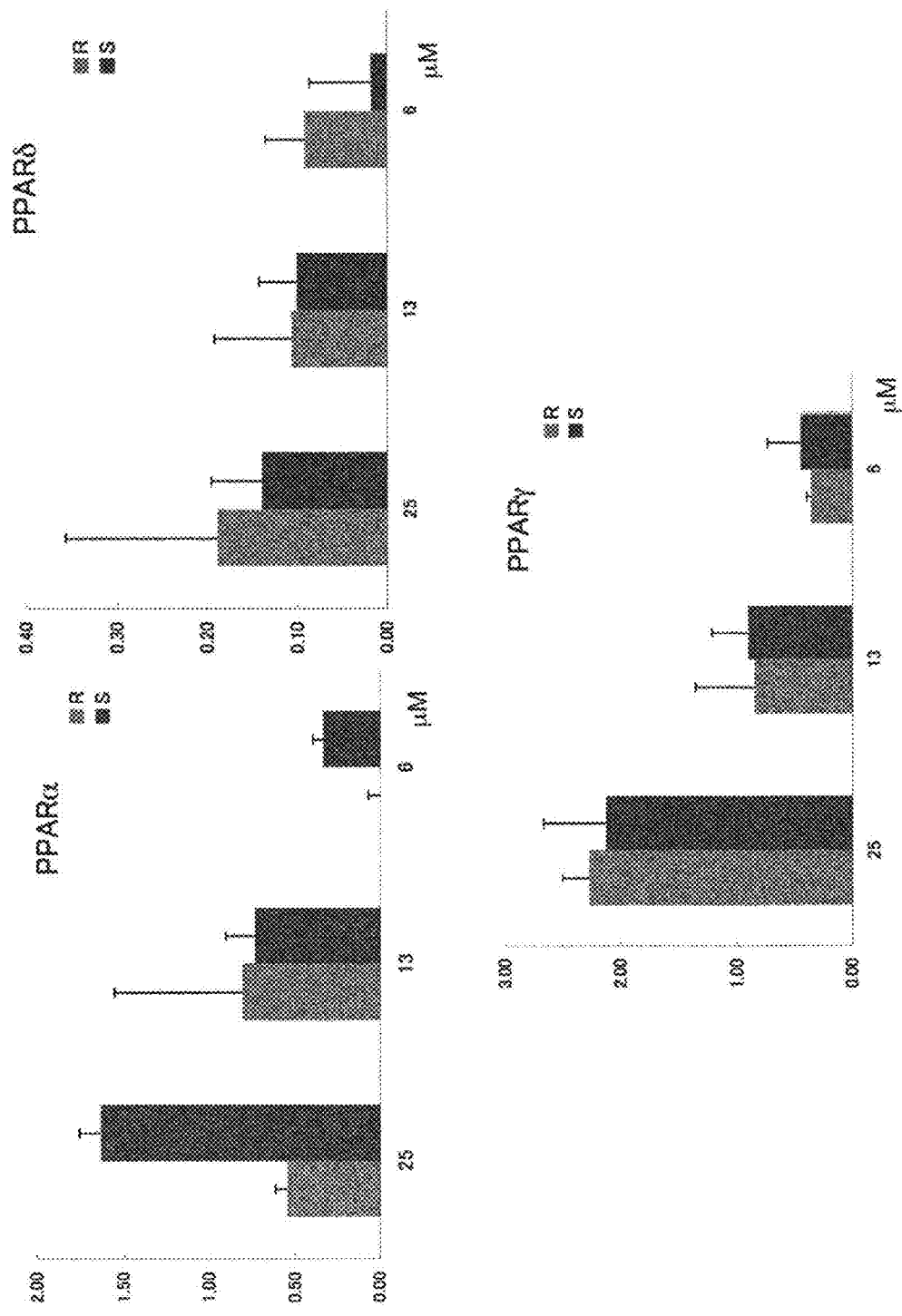
FIG. 6 is a graph comparing activities by the difference in the stereo-structure of the compound of Chemical formula 9

Furthermore, regarding C10, it was verified whether the difference of the spatial structure affected the activity. C10 has R body and S body like Chemical formulae 10 and 11, and in FIG. 6, three PPARs were compared with each other about whether the activities are different depending on the difference of the bodies. The results of three tests were averaged. As a result, it could be verified that there was no significant difference between activities of the R body and the S body. Thus, C10 is useful for efficient manufacture, because the spatial structure need not be taken into consideration in the manufacture. In relation to PPARα, there is a significant difference between values of the R and S bodies in the case of 25 μM, and the reason may be that a difference in any toxicity affected the values. Also, since C9 and C11 respectively have a structure that the number of the side chains differs from that of C10 by only 1 chain, it is considered that the difference in the spatial structure does not affect the activity like C10.

[Chemical formula 10]

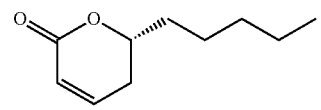

(R)-6-pentyl-5,6-dihydro-2H-pyran-2-one

[Chemical formula 11]

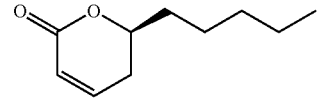

(S)-6-pentyl-5,6-dihydro-2H-pyran-2-one

A synthesis method of Chemical formula 11 is as below.

A solution of diisopropylamine (1.1 ml, 7.7 mmol) in THF (33 ml) was cooled to −78° C. under a nitrogen atmosphere, to which a butyllithium-hexane solution (1.0 M, 6.5 ml, 8.0 mmol) was added, and 10 minutes later, a solution of 6-pentyltetrahydro-2H-pyran-2-one (10S) (1.0 g, 5.9 mmol) in THF (2 ml) was dropped, and stirred for 10 minutes. Subsequently, a solution of phenylselenyl chloride (1.2 g, 6.2 mmol) in THF (5 ml) was slowly dropped, and stirred at −78° C. for another 30 minutes, to which a saturated ammonium chloride solution was slowly dropped to terminate the reaction. The reaction mixture was extracted with ether, and its organic layer was dried with anhydrous sodium sulfate and distilled off under reduced pressure. When the residue was purified by a silica gel column chromatography (hexane-ethyl acetate 10:1-8:1-6:1), a pure phenylselenide (10S-M) (1.4 g, 78%) was obtained. A solution of phenylselenide (1.4 g, 2.7 mmol) in THF (14 ml) was cooled to 0° C., to which sodium bicarbonate (720 mg, 8.6 mmol) was added, and 30% hydrogen peroxide water (2.4 g, 70.0 mmol) was slowly dropped while stirring. This was stirred at 0° C. for another one hour, to which a sodium thiosulfate aqueous solution was added to terminate the reaction. The reaction mixture was extracted with chloroform, then its organic layer was dried with anhydrous sodium sulfate and distilled off under reduced pressure. When the residue was purified by a silica gel column chromatography (hexane-ethyl acetate 5:1-4:1), a pure (S)-6-pentyl-5,6-dihydro-2H-pyran-2-one (10S-D) (342 mg, 47%) was obtained.

Note that the synthesis of (R)-6-pentyl-5,6-dihydro-2H-pyran-2-one (10R-D) of Chemical formula 10 conforms to the above method.

Data on apparatus for Chemical formula 10 and Chemical formula 11 is as below.

(Chemical Formula 10)

colorless oil; $[\alpha]^{25}_D$: −76.0° (c=0.1, CHCl$_3$); $^1$H-NMR (400 MHz, CDCl$_3$)δ: 0.90 (3H, t, J=6.8 Hz), 1.32 (4H, m), 1.41 (1H, m), 1.52 (1H, m), 1.65 (1H, m), 1.80 (1H, m), 2.34 (2H, m), 4.43 (1H, m), 6.02 (1H, dt, J=9.6, 1.7 Hz), 6.89 (1H, m); ESIMS (positive ion mode): m/z 191.0972[M+Na]$^-$.

(Chemical Formula 11)

colorless oil; $[\alpha]^{25}_D$: +112.6° (c=0.1, CHCl$_3$); $^1$H-NMR (400 MHz, CDCl$_3$)δ: 0.90 (3H, t, J=7.0 Hz), 1.32 (4H, m), 1.41 (1H, m), 1.52 (1H, m), 1.65 (1H, m), 1.80 (1H, m), 2.34 (2H, m), 4.42 (1H, m), 6.02 (1H, dt, J=10.0, 1.5 Hz), 6.89 (1H, m); ESIMS (positive ion mode): m/z 191.0974[M+Na]$^-$.

INDUSTRIAL APPLICABILITY

The drug of the present invention can be obtained by synthesis, while its molecular weight is relatively small, its synthesis method is not complex, and it can be stably provided as a medicine. Therefore, its industrial utility is high.

What is claimed is:

1. A method of enhancing PPARα, γ and δ agonist activities in vertebrates, the method comprising: providing a composition comprising an effective amount of active ingredient in a biologically acceptable medium, the active ingredient comprising a compound having a chemical formula selected from the group consisting of:

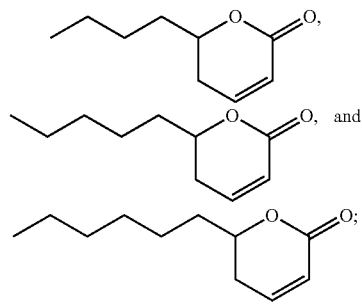

and administering the composition to a vertebrate.

2. The method of claim 1, wherein the compound has the chemical formula:

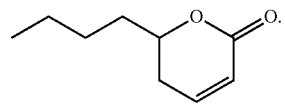

3. The method of claim 1, wherein the compound has the chemical formula:

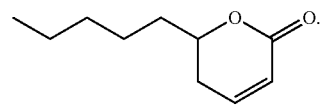

4. The method of claim 1, wherein the compound has the chemical formula:

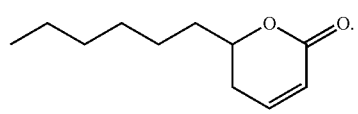

5. The method of claim 1, wherein the vertebrate is a human.

6. The method of claim 1, wherein administering comprises orally administering the composition.

7. The method of claim 6, wherein the composition is a tablet, a granule, a powder, or a capsule.

8. The method of claim 1, wherein the composition comprises a concentration of about 5 μM to about 50 μM of the active ingredient.